United States Patent [19]

Carr et al.

[11] Patent Number: 4,600,791
[45] Date of Patent: Jul. 15, 1986

[54] PROCESS FOR PREPARATION OF PHOSPHAZENE ESTERS

[75] Inventors: Lawrence J. Carr, Elk Grove Village; George M. Nichols, Evanston, both of Ill.

[73] Assignee: Borg-Warner Chemicals, Inc., Parkersburg, W. Va.

[21] Appl. No.: 560,096

[22] Filed: Dec. 12, 1983

[51] Int. Cl.$^4$ .............................................. C07F 9/24
[52] U.S. Cl. .................................................... 558/80
[58] Field of Search ........................................ 260/973

[56] References Cited

U.S. PATENT DOCUMENTS 3,304,350 2/1967 Kober et al. .................. 260/973
3,972,887 8/1976 Freedman ...................... 260/973
4,327,040 4/1982 Arend et al. .................. 260/973

FOREIGN PATENT DOCUMENTS 1227144 4/1971 United Kingdom ............... 260/968

OTHER PUBLICATIONS

Austin et al., "Jou. Macromolecules", vol. 16, No. 5, (1983), pp. 719-722.
Walsh et al., "Inorganica Chemica", vol. 16, (1976), L9-L10.
Product brochure from Elmontechem, Pasadena, Calif.
Singer et al., "Syn. & Eval. of Phosphazene Fire Resistant Fluids", Dept. of Navy (1982).
Allcock, "Phosphorus-Nitrogen Compounds", (1972), pp. 165-166.
Shaw et al., "The Phosphazenes", Chem. Reviews 62(3) (1962), pp. 267-269.
Allcock, "Heteroatom Ring Systems and Polymers", (1967), p. 236.
Kirk-Othmer, vol. 1, (1963), p. 600.
Dehmlow et al., "Phase Transfer Catalysis", (1980, p. 77).

Primary Examiner—Anton H. Sutto
Attorney, Agent, or Firm—Emily A. Richeson

[57] ABSTRACT

A process for the preparation of certain phosphazene esters. The process is characterized by its utilization of a phase transfer catalyst, which may be either a quaternary ammonium compound or a quaternary phosphonium compound.

11 Claims, No Drawings

PROCESS FOR PREPARATION OF PHOSPHAZENE ESTERS

This invention relates as indicated to a process for preparing certain phosphazene esters. More particularly, it relates to such a process which is characterized by its utilization of phase transfer catalysis.

BACKGROUND OF THE INVENTION

In phase transfer catalysis a reactant in a liquid organic phase ordinarily is reacted with a second reactant in another phase, usually aqueous, the reaction being catalyzed by a so-called phase transfer catalyst. The phase transfer catalyst acts to solubilize or extract inorganic and organic ions, in the form of ion pairs, into the organic phase. Without such a catalyst the desired reaction would be slow or might not occur at all.

U.S. Pat. No. 4,290,977 (Hucks et al.) shows the preparation of neutral phosphoric acid esters by the method of phase interface condensation. Phosphorus oxychloride, for example, is reacted with phenol in a mixture of water and toluene which also contains sodium hydroxide. The reaction is carried out at 25°–30° C. for a period of 20 minutes. The yield of "pure product" is said to be virtually quantitative. A stoichiometric excess of phenolic reactant is required in the reaction.

U.S. Pat. No. 3,836,608 (Franko-Filipasic et al.) shows the reaction of phosphonitrilic chloride polymers with an alcohol or alkoxide to produce a partially chlorinated ester. The partially chlorinated ester then is heated to form a condensed polymeric system by eliminating alkyl halide while forming P—O—P bonds. The preferred temp for the latter reaction is 130° to 220° C. The use of linear polymers in the reaction is preferred. The preferred temperature range for the reaction is 130°–220° C. All of the illustrative examples of the process show the reaction of sodium propoxide with a stoichiometric excess of phosphonitrilic chloride.

The reaction of sodium 4-nitrophenate with dimethoxythiophosphoryl chloride is shown to be catalyzed efficiently by a mixture of N-methylimidazole and a quaternary salt (TBAB) at page 94 of "Phase Transfer Catalysis in Organic Synthesis", Weber et al., Springer-Verlag, 1977. Also, at page 256 of this same text there is shown the "normally difficult nucleophilic displacement on hexachlorocyclotriphosphazene" facilitated by 18-crown-6 ether. "Crown ethers" are sometimes used as phase transfer catalysts.

"Phase Transfer Catalysis", Dehmlow et al., Verlag Chemie, 1980, at page 77, shows the reaction of a dialkyl phosphite with carbon tetrachloride and an alcohol in 50% aqueous sodium hydroxide to give a trialkyl phosphate. Benzyltriethylammonium chloride (TEBA) is used as a catalyst. The reaction is illustrated by the following equation

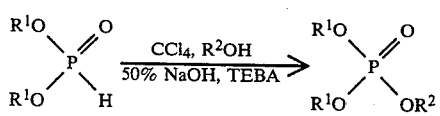

The reaction of dichlorophosphazene trimer with sodium trifluoroethoxide is shown at page 152 of "Phosphorus-Nitrogen Compounds", Allcock, Academic Press, New York (1972).

SUMMARY OF THE INVENTION

The invention of the present application is a process for the preparation of phosphazene esters comprising reacting a dichlorophosphazene polymer with a phenol, a polyfluoroalkanol, or mixtures thereof, in a medium comprising a mixture of water, a base, a water-immiscible solvent and a phase transfer catalyst (PTC). The process is especially useful in the preparation of oligomeric phosphazene esters.

The process is illustrated by the following equation

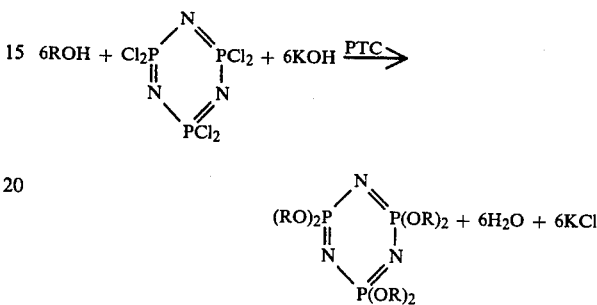

where R is, for example, a phenyl ring.

DETAILED DESCRIPTION OF THE INVENTION

Dichlorophosphazene polymers may be prepared by the reaction of ammonium chloride with phosphorus pentachloride in a chlorinated hydrocarbon solvent. Particularly preferred processes, with experimental details, may be found in U.S. Pat. No. 3,347,643 (Nielsen); U.S. Pat. No. 3,407,047 (Paddock et al.); U.S. Pat. No. 3,462,247 (Paddock et al.); U.S. Pat. No. 3,667,922 (Proctor et al.); and U.S. Pat. No. 3,367,750 (Jaszka et al.). The disclosures of these patents are incorporated herein by reference.

As indicated in the above patents, preparation of the cyclic trimer invariably results in a product which contains varying proportions of higher cyclic and linear oligomers. For purposes of the present invention it is convenient to discuss the use of relatively pure cyclic trimer, which can be obtained by crystallization from a solvent such as petroleum ether. It is to be understood, however, that the process of this invention works equally well with the higher cyclic dichlorophosphazene oligomers such as tetramer, pentamer, etc., and also for linear polymers, i.e., $(PNCl_2)_n$, where n may be as high as $10^4$ or more.

The phenol reactant may be phenol itself or it may be a substituted phenol. Substituted phenols include alkylphenols, halophenols and haloalkylphenols such as, for example, o-cresol, m-cresol, p-cresol, o-ethylphenol, p-ethylphenol, 4-n-octylphenol, 4-decylphenol, 4-(2-ethylhexyl)phenol, 2,4-ditertiarybutylphenol, 4-n-butyl-2-methylphenol, 2,4,6-trimethylphenol, 3-(trifluoromethyl)phenol, 4-(chloromethyl)phenol, 4-(dibromomethyl)phenol, 4-(chloroethyl)phenol, 2-(1-fluoroethyl)phenol, p-chlorophenol, p-bromophenol, and the like. Dihydricphenols likewise are contemplated, e.g., resorcinol, hydroquinone, 4-n-butylresorcinol and 3-sec-butylcatechol. In the case of alkylphenols the alkyl group may contain 1–18 carbon atoms; in the case of haloalkylphenols, the alkyl group may contain 1–6 carbon atoms.

The polyfluoroalkanol may have 2–15 carbon atoms and up to 28 fluorine atoms. Illustrative examples include trifluoroethanol, heptafluoropropanol-1, hexafluorobutanol-1, decafluorohexanol-1, dodecafluoroheptanol-1, 2,2,3,3,4,4-hexafluoro-1,5-pentanediol, etc. Most of the polyfluorinated alkanols contemplated herein conform to the structure $H(CF_2)_nCH_2OH$ wherein n is 2–14, although fluorinated gycols are also contemplated. The presence of the fluorine atoms on the carbon atom immediately adjacent the carbinol group imparts a degree of increased acidity which permits the carbinol group to react with the dichlorophosphazene polymer.

The base employed in the process preferably is an alkali metal base such as sodium hydroxide or potassium hydroxide. Alkaline earth metal bases, however, may be used, e.g., calcium hydroxide, barium hydroxide and magnesium hydroxide. Potassium hydroxide is particularly preferred.

The water-immiscible solvent should also be aprotic so as to preclude hydrogen bonding to the anions in the reaction mixture. The solvents should also be relatively low-boiling, i.e., below about 200° C., and preferably below about 150° C., so as to permit easy removal from the desired reaction product. It should also be relatively inert in the reaction medium. Illustrative examples of suitable solvents include chlorobenzene, methylene chloride, chloroform, carbon tetrachloride, ethyl chloride, ethylene dichloride, 1,2,2-trichloroethane, 1,1,2,2-tetrachloroethane, trimethylene dichloride, tetramethylene dichloride, 1,2,3-trichloropropane, cis-1,2-dichloroethylene, o-dichlorobenzene, bis-(2-chloroethyl) ether and diethyl ketone.

The phase transfer catalyst is a quaternary salt having the structure $R_4AX$ wherein the R's are the same or different alkyl, aryl, or aralkyl groups, A is nitrogen or phosphorus, and X is Cl, Br, I, F, OH, $HSO_4$, $NO_3$, $BH_4$, $IO_4$, $ClO_4$, CN, $N_3$, $OCH_3$, tosylate, or benzoate. These alkyl, aryl and aralkyl groups may contain 1–18 carbon atoms. Suitable illustrative quaternary salts include tetrabutylphosphonium bromide, tetrabutylammonium bromide, benzyltriethylammonium chloride, tricaprylmethylammonium chloride, benzyltriethylammonium bromide, tetrabutylammonium chloride, cetyltrimethylammonium bromide, tetra-n-butylammonium chloride, tetra-n-hexylammonium chloride, benzyltriphenylphosphonium chloride, triphenyl-n-propylphosphonium bromide and tetrabutylphosphonium chloride. Preferably X is chlorine or bromine.

The prior art teaches the use of sodium flouroalkoxides to make fluoroalkoxyphosphazene esters. The process of this invention eliminates the need to make the sodium fluoroalkoxides which can be hazardous to handle in large quantity as noted by Allcock on page 152 of "Phosphorus-Nitrogen Compounds", Academic Press (1972).

The process is carried out at a temperature within the range of from about 0° C. to about 150° C. A particularly preferred range is from about 10° C. to about 125° C.

Ordinarily, separate solutions of the phosphonitrilic chloride trimer in the organic solvent, and the phenol or alcohol in aqueous solution, are prepared and the one added to the other, followed by heating at the desired temperature until the reaction is finished. The reactants, catalyst, solvent, etc. may, however, be mixed in any order without significant detriment to the desired reaction.

The reactants are used in stoichiometric quantities. A slight excess of either may be used depending on their relative availability and cost. From about 1% to about 20%, on a molar basis, of phase transfer catalyst is used; this amount is based on the number of chlorine equivalents of dichlorophosphazene polymer. It appears that a larger proportion of catalyst facilitates a more complete reaction, i.e., as indicated by a product having a lower residual chlorine content.

Approximately one mole of base is used per chlorine equivalent of the dichlorophosphazene polymer. This amount is of course dictated by the stoichiometry of the reaction by which the hydrogen chloride resulting as a by-product is obtained as potassium chloride, for example.

The amounts of water and water-immiscible solvent are not critical so long as each is used in sufficient quantity to dissolve the dichlorophosphazene polymer and the phenol or polyfluoroalkanol.

EXAMPLE 1

To a solution of 28.2 g. (0.30 mol) of phenol, 16.83 g. (0.30 mol) of potassium hydroxide and 6.0 g. (0.018 mol) of tetrabutylphosphonium bromide in 120 ml. of water 25° C. there is added a solution of 17.4 g. (0.05 mol) of dichlorophosphazene trimer $[(PNCl_2)_3]$ in 100 ml. of chlorobenzene. The mixture is stirred at 25°–30° C. for three hours, then heated at 95° C. for 21 hours with continued stirring. The cooled product mixture consists of two colorless layers. The lower, organic layer is isolated, washed with 5% aqueous hydrochloric acid, then with 5% aqueous sodium bicarbonate and dried. The dry solution is stripped to a white crystalline solid shown by GLC analysis to be 95.8% pure $[NP(OC_6H_5)hd\ 2]_3$. The yield is 92.7% of the theory. Elemental analyses corroborate this structure.

EXAMPLE 2

To a solution of 16.83 g. (0.3 mol) of potassium hydroxide, 30.0 g. (0.3 mol) of trifluoroethanol and 5,8 g. (0.018 mol) of tetrabutylammonium bromide in 120 ml. of water there is added 17.4 g. (0.05 mol) of dichlorophosphazene trimer $[(PNCl_2)_3]$ in 100 ml. of chlorobenzene. The resulting mixture is stirred at 70° C. for 21 hours whereupon the organic layer is isolated, washed with 5% aqueous sodium hydroxide, then with 5% aqueous hydrochloric acid, and finally with 5% aqueous sodium bicarbonate. The dry product is filtered and stripped to a white crystalline residue weighing 33.3 g. (91.3% of the theory). Elemental analyses confirms its identity as the desired hexakis-(trifluoroethoxy)cyclotriphosphazene.

EXAMPLE 3

To a stirred solution of 17.4 g. (0.05 mol) of dichlorophosphazene trimer $[(PNCl_2)_3]$ and 5.8 g. (0.018 mol) of tetrabutylammonium bromide in 120 ml. of chlorobenzene purged with nitrogen, there is added a solution of 14.1 g. (0.15 mol) of phenol and 8.42 g. (0.15 mol) of potassium hydroxide in 60 ml. of water. The addition is made portionwise over a period of 28 minutes. The resulting mixture is heated at 70° C. for five hours, then cooled to 21° C. and treated with continued stirring with a solution of 16.5 g. (0.165 mol) of trifluoroethanol and 8.42 g. (0.15 mol) of potassium hydroxide in 60 ml. of water. This mixture is heated at 70° C. for 16 hours, then cooled, and the organic layer isolated and washed with 5% aqueous sodium hydroxide, then with 5% aqueous hydrochloric acid, dried and filtered. The filtrate is stripped free of solvent leaving 29.16 g. (82% of the theory) of a white crystalline solid. Elemental analyses shows it to be the desired mixed phosphazene ester.

EXAMPLE 4

To a stirred mixture of 14.1 g. (0.15 mol) of phenol, 15.0 g. (0.15 mol) of trifluoroethanol, 16.83 g. (0.30 mol) of potassium hydroxide and 120 ml. of water, purged with nitrogen, there is added a solution of 17.4 g. (0.05 mol) of dichlorophosphazene trimer [(PNCl$_2$)$_3$] and 5.8 g. (0.018 mol) of tetrabutylammonium bromide in 100 ml. of chlorobenzene. The addition is made over a period of 42 minutes at a temperature of 31°–50° C. The resulting mixture is heated at 70° C. for 28 hours. During the last six hours of this period an additional 3.0 g. of trifluoroethanol, 1.4 g. of phenol and 3.0 g. of potassium hydroxide are added. The product mixture is cooled and treated as in Examples 1–3 yielding 30.0 g. (84.4% of the theory) of an almost colorless, clear liquid. Elemental analyses show it to be the desired mixed ester.

EXAMPLE 5

A solution of 16.83 g. (0.30 mol) of potassium hydroxide, 30.0 g. (0.30 mol) of trifluoroethanol and 5.8 g. (0.0.18 mol) of tetrabutylammonium bromide in 120 ml. of H$_2$O is purged with nitrogen for 30 minutes, then treated with a solution of 17.4 g. (0.30 chlorine equivalents) of dichlorophosphazine oligomer* in 100 ml. of chlorobenzene at 22°–44° C. throughout a period of 47 minutes. The resulting mixture then is heated with stirring at 70° C. for four hours. The cooled mixture separates into three layers. The top layers (water and chlorobenzene) are treated with 150 ml. of ether, washed with 5% aqueous sodium hydroxide, with 5% hydrochloric acid, and finally with 5% aqueous sodium bicarbonate. The washed ether solution is dried over magnesium sulfate and stripped to a brown liquid residue weighing 5.03 g. The bottom layer is dissolved in 100 ml. of ether, washed, dried and stripped as above, yielding 26.08 g. of a viscous liquid residue. The combined (5.03 g. plus 26.08 g.) yield of product is 85.3% of the theory. Elemental analysis, including a chlorine content of 0.23%, corroborates the structure of the desired phosphazene ester.

*A mixture of oligomers (PNCl$_2$)$_n$ where n is 3 to 22

All parts and percentages herein are by weight unless otherwise specifically states.

We claim:

1. A process for the preparation of phosphazene esters comprising reacting a dichlorophosphazene with a hydroxyl reactant which is a phenol, a polyfluoroalkanol, or mixtures thereof, in a medium comprising a mixture of water, a base, a water-immiscible solvent and a phase-transfer catalyst.

2. The process of claim 1 wherein the phase transfer catalyst is one having the structure:

$$R_4AX$$

wherein the R's are the same or different alkyl, aryl or aralkyl group, A is nitrogen or phosphorus, and X is halogen, OH, HSO$_4$, NO$_3$, BH$_4$, IO$_4$, ClO$_4$, CN, N$_3$, OCH$_3$, tosylate or benzoate.

3. The process of claim 1 wherein the phase transfer catalyst is one having the structure:

$$R_4AX$$

wherein X is bromine or chlorine.

4. The process of claim 2 wherein A is nitrogen.

5. The process of claim 2 wherein A is phosphorus.

6. The process of claim 2 wherein R is alkyl.

7. The process of claim 2 wherein R is benzyl.

8. The process of claim 2 wherein the R's are a mixture of alkyl and aralkyl groups.

9. The process of claim 1 wherein substantially stoichiometric proportions of dichlorophosphazene trimer and phenol or trifluoroethanol are reacted.

10. The process of claim 1 wherein the hydroxyl reactant is phenol.

11. The process of claim 1 wherein the hydroxyl reactant is trifluoroethanol.

* * * * *